(12) United States Patent
Kekki

(10) Patent No.: US 7,399,622 B2
(45) Date of Patent: Jul. 15, 2008

(54) PROCESS FOR THE EXTRACTION OF β-AMYLASE

(75) Inventor: Pekka Kekki, Forssa (FI)

(73) Assignee: Danisco Sugar Oy, Kantvik (FI)

( * ) Notice: Subject to any disclaimer, the term of this patent is extended or adjusted under 35 U.S.C. 154(b) by 645 days.

(21) Appl. No.: 10/635,183

(22) Filed: Aug. 6, 2003

(65) Prior Publication Data

US 2004/0067570 A1 Apr. 8, 2004

Related U.S. Application Data

(63) Continuation-in-part of application No. PCT/FI02/00070, filed on Jan. 30, 2003.

(51) Int. Cl.
*C07K 1/14* (2006.01)
*C12N 9/32* (2006.01)

(52) U.S. Cl. .................. 435/204; 435/183; 435/267; 435/272

(58) Field of Classification Search ............. 435/201, 435/200, 209, 272, 275, 267
See application file for complete search history.

(56) References Cited

U.S. PATENT DOCUMENTS

| 3,492,203 A | 1/1970 | Mitsuhashi et al. |
| 4,647,538 A | 3/1987 | Zeikus et al. |
| 4,675,296 A | 6/1987 | Lehmussaari |
| 4,914,029 A | 4/1990 | Caransa et al. |
| 4,970,158 A | 11/1990 | Outtrup et al. |
| 5,066,218 A | 11/1991 | Silver |
| 5,294,341 A | 3/1994 | Fukazawa |

FOREIGN PATENT DOCUMENTS

| FI | 61516 | 4/1982 |
| FI | 79858 | 11/1989 |
| JP | 60 027 383 | 2/1985 |
| JP | 60 126 080 | 7/1985 |
| JP | 63 079 590 | 4/1988 |
| JP | 63 248 389 | 10/1988 |

OTHER PUBLICATIONS

Marinchenko et al (Appl. Biochem. Microbiol. 15(6):670-673 (1979)).*
International Preliminary Examination Report for PCT/FI02/00070.*
Buttimer, et al., "Mechanisms of the Release of Bound β-Amylase", *Journal of the Institute of Brewing*, 106(2) 83-94 (2000).

* cited by examiner

*Primary Examiner*—Sandra Saucier
*Assistant Examiner*—Aaron J Kosar
(74) *Attorney, Agent, or Firm*—Scully, Scott, Murphy & Presser, P.C.

(57) ABSTRACT

The invention relates to a process for extracting beta-amylase from cereal by means of cellulase. The invention further relates to the use of cellulase in the extraction of β-amylase.

26 Claims, 1 Drawing Sheet

PROCESS FOR THE EXTRACTION OF β-AMYLASE

CROSS REFERENCE TO RELATED APPLICATIONS

This application is a continuation-in-part of International Patent Application No. PCT/FI02/00070 filed on Jan. 30, 2003.

FIELD OF THE INVENTION

The present invention relates to enzyme technology. More precisely, the invention relates to a process for extracting β-amylase from cereal and to the use of an enzyme in the extraction.

BACKGROUND OF THE INVENTION

β-amylase is a starch-degrading enzyme which hydrolyzes alpha-1,4 bonds. It is found, e.g., in bacteria and plants and it breaks down starch mainly into maltose at the non-reducing end of the starch chain. β-amylase is abundant, e.g., in grains, where it converts the nutrient store of the cereal, i.e., starch, into sugar, if necessary. In cereals starch is mainly stored in the form of amylose and amylopectin. β-amylase converts all of the amylose into maltose, whereas about 60% of the amylopectin is converted into maltose and the rest into dextrin.

β-amylase is a commercially significant enzyme which is used, e.g., in the starch industry to produce maltose. Products containing large amounts of maltose are used e.g. in the confectionery and food industry. β-amylase has been isolated both from bacteria and from plants. For example, it has been obtained from *Bacillus* bacteria (U.S. Pat. No. 4,970,158 and JP Patent No. 60,126,080) and from thermostable *Clostridium* bacteria (U.S. Pat. No. 4,647,538). In addition to maltose, β-amylases derived from bacteria produce considerable amounts of maltotriose, whereas plant-based β-amylases produce relatively more maltose and thus they are more suitable for processes where the purpose is to obtain as sweet and/or fermentable products as possible. Besides, large-scale production of β-amylase from bacteria is difficult. The β-amylase used in industry is plant-based, in which case usually cereal, particularly barley or wheat, but also soybeans are used as the enzyme source.

During the growth, β-amylase is formed in the grains, where it is stored. A grain consists of a germ and a starch-containing endosperm, i.e. a kernel, which are separated from each other by a scutellum. The endosperm is surrounded by an aleutrone layer and the whole grain is surrounded by a pericarp layer, a testa layer and the actual husk. Wheat has no proper husk, but the pericarp and testa form a hard outer shell. β-amylase accumulates mainly in the endosperm and scutellum. The largest amounts of β-amylase are found in the outermost portions of the endosperm immediately underneath the aleurone layer.

β-amylase of barley has been studied thoroughly. This β-amylase and its production are described, e.g., in the following publications: D. E. Briggs, *Barley*, Chapman & Hall, London, 1978; Cook, *Barley and Malt*, Academic Press, London, 1962; J. R. A. Pollock, *Brewing Science*, Academic Press, London, 1979. The systematic name of the enzyme is 1,4-alpha-D-glucan maltohydrolase (Enzyme Classification ("EC") 3.2.1.2). In the past, the β-amylase of cereal was separated first by grinding or milling the grain and then by extracting the β-amylase with water or a buffer. Purification of enzyme from extract of this kind is naturally difficult and laborious because, in addition to the enzyme concerned, the extract contains several other soluble components of the grain. Attempts have been made to improve separation of β-amylase from a solution containing it, e.g., by adsorbing the enzyme with polymer in the presence of ammonium sulphate (U.S. Pat. No. 5,294,341). Release of β-amylase from gluten has been experimented with protease (JP Patent No. 63,079,590).

β-amylase has also been isolated from the waste liquid of wheat starch production by adding sodium alginate and by recovering the coagulated enzyme (JP Patent No. 60,027, 383) or by forming a calcium phosphate gel to which the enzyme adsorbs and from which it is then recovered (JP Patent No. 63,248,389). Waste liquid from starch production is not a good source of β-amylase because it is very dilute and contains large amounts of other components, which makes purification and concentration difficult and, as a result, the yield is low.

To obtain a purer raw extract and to avoid difficult downstream processing, it has been suggested that β-amylase be extracted from whole or partly husked grains. When e.g. barley grains are husked in such a manner that their endosperm does not break, the outmost layers of the endosperm function as a kind of filter which prevents access of insoluble substances to the steep water and restricts the access of soluble substances. It is preferable to carry out extraction in the presence of a reducing substance which releases β-amylase from other proteins of the grain (FI Patent No. 61,516 and U.S. Pat. No. 4,675,296).

A process for extracting β-amylase from cereal which reduces the cereal extraction time and improves the yield of enzyme has now been invented. The process is simple to carry out and is particularly suitable for processing husked cereal, which also facilities further purification of the enzyme.

SUMMARY OF THE INVENTION

The present invention provides a method for extracting β-amylase comprising extracting cereal in the presence of cellulase in an aqueous medium to obtain an extract containing β-amylase. The invention further provides a method of using cellulase in the extraction of β-amylase from cereal.

Cellulase is used, e.g., in the production of starch from milled cereal to reduce the viscosity of slurry and to separate starch from protein. It has now been surprisingly found in accordance with the present invention that addition of cellulase to the extraction water of β-amylase improves the yield of β-amylase and allows reduction of the extraction time.

In one aspect of the present invention, grains for extraction of β-amylase are husked so that the actual husk is removed but the endosperm of the grain is left substantially intact.

In another aspect of the present invention, the extraction of β-amylase is conducted in an aqueous medium under reducing conditions.

In a further aspect of the present invention, the cellulase enzyme employed in the present invention comprises an enzyme preparation having at least cellulase, hemicellulase and β-glucanase activities.

DETAILED DESCRIPTION OF THE INVENTION

Figure 1:
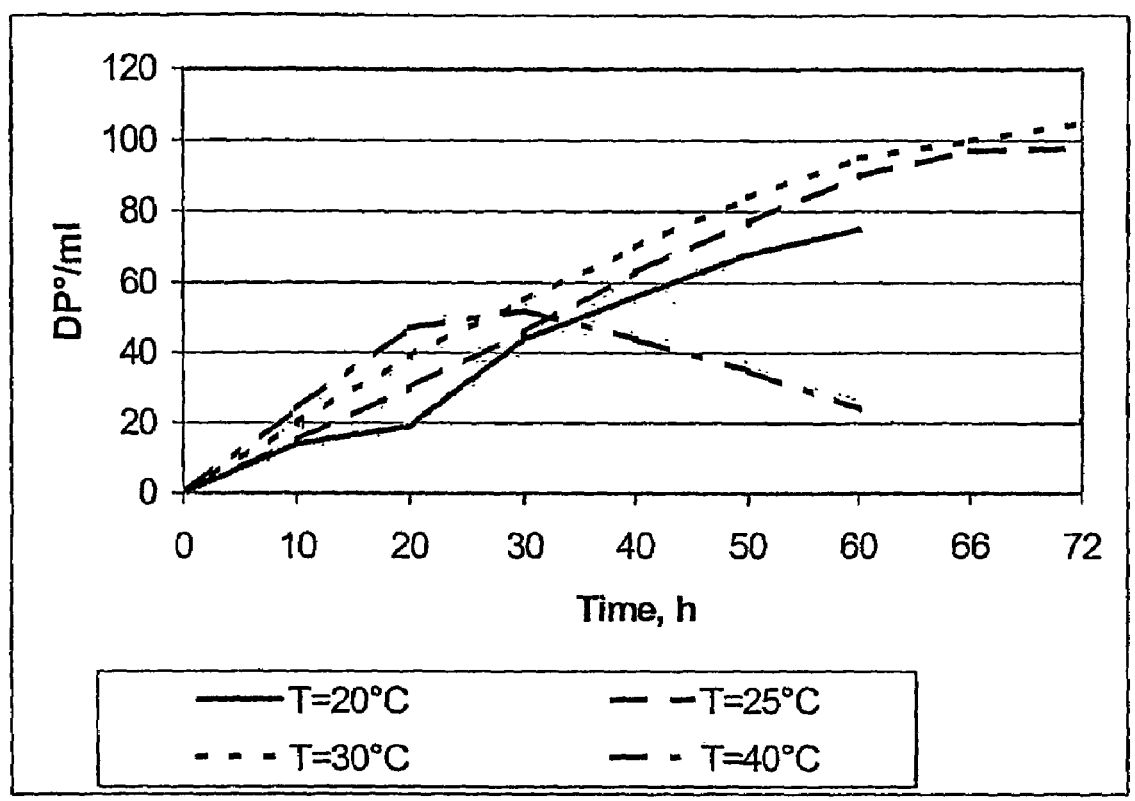
FIG. 1 shows the influence of temperature on the yield of β-amylase as a function of time.

The present invention is directed to a method for extracting β-amylase comprising extracting cereal in the presence of cellulase in an aqueous medium to obtain an extract containing β-amylase. The β-amylase can readily be recovered from the medium. The invention further provides a method of using cellulase in the extraction of β-amylase from cereal.

According to the present invention, the process of the present invention is employed for extraction of β-amylase from different cereals, e.g., wheat, barley, rye and soya. Preferably, the present invention is directed to extracting β-amylase from wheat and rye and particularly, from barley.

In accordace with the present invention, β-amylase is isolated from ungerminated grains which do not contain significant amounts of enzymes other than β-amylase. According to the present invention, β-amylase can be extracted from unhusked grains but it is preferably extracted from husked, milled, ground or polished grains. It is advisable to husk rye and barley in accordance with the present process. The best results are achieved by extracting husked barley grains.

In one embodiment of the present invention, to prevent access of starch from the grain endosperm to the extract, husking has to be carried out so as not to disrupt the actual living grain. However, the actual husk has to be removed as carefully as possible. The reason for this is that the husk is so dense that it hinders penetration of β-amylase. Husked barley thus means barley from which the actual husk of the grain has been removed but the endosperm is left intact. In practice, this means that at most about 20% of the weight of an unhusked grain is removed by husking. Usually 10 to 20% is removed as husk material. In that case the outermost layers (pericarp, testa and aleurone layer) of the endosperm function as a kind of ultra filter which prevents access of insoluble substances and substantially also that of soluble substance to the extraction water. The extract obtained from grains processed this way is relatively pure, which facilitates further processing, such as purification and concentration of the enzyme. Processes generally known in the enzyme industry, such as pressure filtering and ultra filtering, can be employed in further processing.

In another embodiment of the present invention, cereal is extracted in an aqueous medium, such as water, or possibly in a buffer solution. During extraction the pH is usually between 6.0 and 6.5. The extraction is preferably carried out in reducing conditions. So much reducing activity is used that the β-amylase bound to the structural protein of the grain is released. The reducing conditions are arranged in a manner known per se in the art, in practice often with $SO_2$, e.g., by addition of sodium metabisulphite and/or sodium sulphite. The ratio of husked grains to the aqueous medium is preferably between 5:8 and 2:3 (weight/volume). The process of the invention is suitable for industrial-scale processes where extraction is carried out in a steel silo, to which e.g. 19 tones of husked barley and 29 $m^3$ of water containing 0.5% of sodium metabisulphite and 0.5% of sodium sulphite are added.

According to the present invention, by extracting barley in the manner described above, an extraction yield including about 45 to 50% of the total β-amylase content of barley can be obtained without separating the water that remains inside the grain. In that case the extraction time is about 72 h. When cellulase is added to the extraction water, as much as 65% of the total amount of β-amylase in the cereal can be extracted while the extraction time decreases to about 60 h.

Cellulose is a linear glucose polysaccharide whose glucose units are linked by β-1,4-glucoside bonds. It is found in cell walls of plants where it is often present together with lignin and hemicellulose. Enzymes that participate in decomposition reactions of cellulose are regarded as cellulases. Cellulases are used industrially e.g. in starch production, paper mass processing, textile processing, degradation of β-glucan in breweries, and in improvement of flour qualities in bakeries. In the process according to the present invention ceullulase breaks down the surface structures underneath any husk of a living grain.

Cellulase is used, e.g. in the production of starch from milled cereal to reduce the viscosity of slurry and to separate starch from protein. It has been surprisingly discovered by the present inventors that addition of cellulase to the extraction water of β-amylase improves the yield of β-amylase and allows reduction of the extraction time. It is thus a principal embodiment of the present invention to extract β-amylase by adding cellulase to the extraction medium.

Commercially available cellulase products are derived either from bacteria, such as the genus *Bacillus*, or from fungi, such as yeasts (e.g. *Saccharomyces*) or moulds. Large amounts of cellulases have been isolated from mould fungi, in particular. The most commonly used cellulase-producing moulds belong to the genera *Humicola, Fusarium, Myceliopthora, Aspergillus, Penicillium* and *Trichoderma*. Some of the production strains have been genetically modified. The present invention preferably employs cellulase derived from mould fungi, in particular from *Trichoderma* moulds.

Commercial enzyme preparations contain several enzyme activities and their amounts and ratios may vary slightly from one manufacturer to another. It is essential for the invention that the cellulase product should contain at least cellulase, hemicellulase and β-glucanase activities. In other words, in this context, cellulase of the present invention refers to an enzyme preparation that decomposes at least cellulose, hemicellulose and β-glucan. All the commercial cellulase products (produced by Genencor International, Röhm Enzymer GmbH and Novo Nordisk) tested by the applicant improved the yield of β-amylase. Cellulase, hemicellulase and β-glucanase activities are described, e.g., in *Novo's Handbook of Practical Biotechnology*, 1986.

Cellulase enzymes can be divided e.g. into endocellulases, exocellulases, exocellobiohydrolases and cellobiases. Endocellulases, i.e., 1,4-β-D-glucan glucanohydreolases, randomly cleave the β-1,4 bonds of cellulose inside the molecule and form oligosaccharides. Exocellulases, i.e., 1,4-β-D-glucan glycohydrolases, cleave β-1,4 bonds at the end of the molecule, releasing glucose. Their effect on the cellubiose is slow. Exocellobiohydrolases, i.e., 1,4-β-D-gucan glucohydrolases, cleave the above-mentioned bonds at the non-reducing end of the molecule, forming cellobiosed, and cellobiases, i.e. β-D-glucoside glucohydrolases, cleave cellobiose into glucose. Hydrolyzation of cellulose into glucose requires endoglucanase (1,4-β-D-glucan glucanohydrolase, EC 3.2.1.4), which cleaves the inside of the molecule and also substituted substrates, but does not degrade crystallized cellulose, cellobiohydrolase (1,4-β-D-glucan cellobiohydrolase, EC 3.2.1.91), which cleaves crystallized cellulose, and β-glucosidase (β-D-glucoside glucohydrolase, EC 3.2.1.21), which is a cellobiase which cleaves cellobiose and cello-oligosaccharides into glucose.

An enzyme group which breaks down hemicellulose, i.e., polysaccharides that are found in nature and contain pentoses, e.g. arabinans, galactans, mannans and xylans, are called hemicellulases. β-glucanases break down β-D-glucans, i.e., glucose polymers that may be branched and contain both β-1,3 and β-1,4 bonds. β-glucane is found, e.g., in cell walls of endosperm cells in grains. Lichenase is endo-β-glucanase (1,3-1,4-β-D-glucan-4-glucanohydrolase) which cleaves the β-1,4 bonds of β-glucane that contains β-1,3 and β-1,4 bonds. Laminarinase (1,3-β-D-glucan-3-glucanohydrolase) cleaves β-glucane that contains only β-1,3 bonds, such as β-1,3 bonds of laminarine-type carbohydrates, and exoglucanase (1,3-β-D-glucan glucohydrolase) cleaves β-1,3 bonds of β-1,3-glucans, forming mainly glucose.

According to the present invention, in extraction of β-amylase, promising results have been achieved with cellulase preparations, e.g., SPEZYME® CE and GC 440 produced by Genencor International. GC 440 is derived from a genetically modified *Trichoderma longibrachiatum* strain and it breaks down cellulose, hemicellulose and β-glucan particularly efficiently. As a product of cellulase enzyme complex, GC 440 contains multiple enzyme activities but is standardized on basis of its activity on carboxymethl cellulose. Detailed assay methods are available from the enzyme provider upon request. The activity of GC 440 enzyme is expressed in Remazol Brilliant Blue-carboxymentyl cellulose ("RBB-CMC") activity units. RBB-CMC activity measures the release of soluble fragments that are dyed with Remazol Brilliant Blue (RBB) and is determined spectrophotometrically against an internal standard. This activity is expressed in International Units (IU). RBB-CMC activity of GC 440 enzyme is at least 1400 IU/g. In addition to the cellulase activity, GC 440 has β-glucanase, β-glucosidase, β-xylosidase, xylanase and acetylesterase activity. These activities are expressed in Units (U) defined by the enzyme provider, i.e., Genencor International. A typical batch of GC 440 contains, on average, approximately 7000 to 9000 U/ml of dinitrosalicylic acid carboxymentyl cellulose ("DNS-CMC") activity, approximately 6000 to 8000 U/ml of β-glucanase, approximately 80 to 90 U/ml of β-glucosidase, approximately 500 to 600 nkat/ml of β-xylosidase, approximately 1700 to 2000 nkat/ml of acetylesterase, approximately 700 to 1400 U/ml of RBB xylanase and approximately 1900 to 2100 U/ml of dinitrosalicylic acid (DNS) xylanase. Very good results have also been achieved using cellulase produced by Röhm Enzyme GmbH, which is sold under the brand name ROHALASE® SEP. The preparation is derived from a *Trichoderma reesei* strain and it contains considerable amounts of β-1,4-endoglucanase activity (at least 4700 CU/g) and xylanase (at least 3000 XylH/g), and smaller amounts of cellobiohydrolase activity. CU and XylH are enzyme activity units used by the enzyme provider, i.e., Röhm Enzyme GmbH. Detailed assay methods are available from Röhm Enzyme GmbH upon request. ROHALASE® SEP also includes β-1,3-glucanase activity, i.e. laminarinase. When the above-mentioned cellulase preparations are used, a suitable amount of the cellulase preparation is at least 0.015%, preferably at least 0.020%, e.g., 0.018 to 0.040, and particularly 0.024 to 0.030% of the weight of cereal.

In case the cellulase preparation GC 440 by Genencor is used as the cellulase preparation, an amount of 0.015% of the weight of the cereal provides, when calculated as enzyme activities, at least 200 IU of RBB-CMC activity per kilogram of cereal, at least 1050 U of DNS-CMC cellulase per kilogram of cereal, at least 900 U of β-glucanase per kilogram of cereal and at least 285 U of DNS-xylanase per kilogram of cereal.

In a further embodiment of the present invention, β-amylase can be extracted in the presence of cellulase at a temperature of 20 to 45° C. The temperature is preferably 25 to 32° C., e.g. 29 to 31° C. The extraction time can be 30 to 72 h, usually at least 48 h, e.g. 48 to 66 h and particularly 55 to 62 h. A suitable extraction time at 30° C. is about 60 h. According to the present invention, after the extraction has been completed, grains, groats or flour are separated from the extraction water using, e.g., a sieve and β-amylase is recovered from the extraction water, from which it is purified and/or concentrated, if desired.

After extraction of β-amylase, the cereal extracted and separated according to the present invention can be used, for producing starch, for example. According to a preferred embodiment of the present invention, β-amylase is extracted and the extract is separated from cereal before the starch is fractionated and separated from the cereal. Alternatively, the β-amylase may be extracted from the cereal matter remaining after removal of starch.

If the enzyme has been extracted from unbroken grains, the extracted grains are first milled, after which the starch production process is carried out in a manner known per se, i.e., the milled grains are mixed into water and the cereal is fractionated utilizing sieving and centrifugal force. During the milling, cellulase is usually added together with β-glucanase to reduce viscosity and separate starch from protein.

The following examples illustrate the invention without limiting it to embodiments disclosed therein.

EXAMPLE 1

Determination of β-Amylase

Before determination of the total amount of β-amylase from cereal, all husk was removed; the dry cereal to be analysed was milled into fine flour and 10 g of the flour was put in a 100-ml Erlenmeyer bottle. 100 ml of 0.5% (weight/volume) sodiumsulphite solution was added and the substances were mixed properly. The mixture was allowed to stay in the bottle for 24 h but it was shaken occasionally. After this it was mixed properly and filtered through a thin filter paper (MN 640 W). The filtrate was diluted in a ration of 1:50 with distilled water and the activity was determined by the method described below. This enzyme assay was also used as such for determining the β-amylase content of extraction solutions in the examples to be described below.

In principle, β-amylase was determined as described in *Food Chemical Codex*, Fourth Edition, 1996, National Academy Press, page 793.

Here a Diastatic Power unit (DP°) is defined as the amount of enzyme in 0.1 ml of a 5% sample dilution that produces an amount of reducing sugars sufficient for reducing 5 ml of Fehling solution from 100 ml of substrate at 20° C. in 1 hour. This method of defining DP° does not correspond to the general definition of DP°.

The enzyme activity was determined by hydrolyzing starch at 20° C., pH 4.6, for 30 minutes. The resulting reducing sugars were determined titrimetically with alkaline ferricyanide. To produce a starch substrate, 20 g (dry substance) of starch (Baker 1130) was mixed with approximately 50 ml of water. Approximately 500 ml of boiling water was added and the mixture was boiled for exactly 2 minutes. 20 ml of acetate buffer (0.5M, pH 4.6) was added to the cooled starch solution and diluted with distilled water to 1 litre. 200 ml of starch substrate tempered to 20° C. was pipetted into a 250-ml volumetric flask. 10 ml of diluted enzyme sample was added and the substances were mixed well. The sample was incubated for exactly 30 minutes in a water bath at 20° C. and 20 ml of 0.5 N NaOH was added. The substances were mixed well and diluted to 250 ml.

10 ml of enzyme dilution and 20 ml of 0.5 N NaOH were pipetted into a 250-ml volumetric flask for a 0-sample. The substances were mixed well and 200 ml of starch substrate was added and diluted to 250 ml. By "0-sample" is meant a sample wherein the enzyme action has been prevented by adding NaOH at the beginning of the incubation time.

0.05 N ferricyanide reagent was prepared by dissolving 16.5 g of potassium ferricyanide ($K_3Fe(CN)_6$) and 22 g of sodiumcarbonate ($Na_2CO_3$) in water and by diluting it to one liter. An A-P-Z solution was prepared by dissolving 70 g of potassium chloride (KCl) and 20 g of zincsulphate ($ZnSO_4 \times 7H_2O$) in 700 ml of distilled water, by adding 200 ml of concentrated acetic acid and by diluting it to one liter. A potassium iodide solution was prepared by dissolving 50 g of potassium iodide (KI) in 100 ml of distilled water and by adding 2 drops of 50% sodiumhydroxide (NaOH). 10 ml of ferricyanide reagent and 5 ml of sample were pipetted into a 250-ml volumetric flask. These were mixed well and heated in a boiling water bath for exactly 20 minutes. The solution was cooled down and 25 ml of A-P-Z reagent and 1 ml of KI solution were added. The mixture was titrated with 0.05 N sodium sulphate solution until the blue color disappeared (dark blue to white).

The β-amylase activity was calculated from the formula $$activity = \frac{(V0 - V1) \times 23 \times K}{100} \; DP°/ml$$

wherein

V0=consumption by 0-sample in titration (ml)

V1=consumption by sample in titration (ml)

K=dilution factor

EXAMPLE 2

The effect of cellulase on the extraction time of β-amylase was studied. β-amylase was extracted from barely without cellulase and with cellulase. 10 kg of barley husked with a husking machine was extracted in 15 liter of water containing 0.5% of sodium metabisulphite and 0.5% of sodiumsulphite. Furthermore, GC440 cellulase produced by Genencor was added to the second batch, the amount of cellulase corresponding to 0.029% of the weight of husked barley. The extraction was carried out at 30° C. The activity of the grain used in extraction was 155 DP°/g, which was determined according to example 1. The results are shown in Tables 1 and 2.

TABLE 1

Extraction without cellulase

| Time, h | β-amylase activity in DP°/ml of extraction solution |
|---|---|
| 10 | 20 |
| 24 | 47 |
| 30 | 55 |
| 48 | 83 |
| 60 | 92 |
| 66 | 98 |
| 72 | 102 |
| 96 | 86 |

TABLE 2

Extraction with cellulase

| Time, h | β-amylase activity in DP°/ml of extraction solution |
|---|---|
| 10 | 23 |
| 24 | 55 |
| 30 | 70 |
| 48 | 92 |
| 60 | 104 |
| 66 | 104 |
| 72 | 100 |
| 96 | 90 |

The results show that addition of cellulase to the extraction water reduces the extraction of β-amylase.

The β-amylase was easily recovered from the extraction solution by pressure filtration and ultra filtration.

EXAMPLE 3

The effect of cellulase on the extraction yield was studied. 10 kg of husked barley with a β-amylase activity of 155 DP°/g was extracted in 15 liter of water containing 0.5% sodium metabisulphite and 0.5% of sodiumsulphite. The extraction was carried out at 30° C. either without cellulase or in the presence of cellulase.

The extraction time without cellulase was 72 h. The total activity of the amount of barley used was 1550 kDP°. 8175 ml of extract with an activity of 95 DP°/ml was obtained by separating the extract with a sieve. The total activity of the extract obtained was thus 776.6 kDP°/ml and the extract yield 50.1%.

A corresponding extraction was carried out in the presence of cellulase by adding an amount of GC440 corresponding to 0.025% of the weight of the husked barley. The extraction time was 60 h. The total activity of the amount of barley used was 1550 kDP°. 9825 ml of extract with an activity of 102° DP/ml was obtained by separating the extract with a sieve. The total activity of the extract obtained was thus 1002.2 kDP°/ml and the extract yield 64.7%.

The results show that addition of cellulase to the extraction water considerably increases the yield of β-amylase.

EXAMPLE 4

The effect of temperature on the extraction of β-amylase was studied. Husked barley was extracted in the manner described in the preceding examples in the presence of cellulase at different temperatures. The dosage of GC 440 cellulase correspond to 0.027% of the weight of the husked barley and the extraction temperature was 20° C., 25° C., 30° C. or 40° C. The results are shown in FIG. 1. The best results were achieved at 30° C.

EXAMPLE 5

The effect of cellulase on the β-amylase yield from wheat was studied. 10 kg of ground wheat with a β-amylase activity of 128 DP°/g was extracted in 15 litres of water containing 0.5% of sodium metabisulphite and 0.5% of sodiumsulphite. The extraction was carried out at 30° C. either without cellulase or in the presence of cellulase.

The extraction time without cellulase was 72 h. The total activity of the amount of what used was 1280 kDP°. 9175 ml extract with an activity of 55 DP°/ml was obtained by separating the extract with a sieve. The total activity of the extract obtained was thus 504.6 kDP°/ml and the extract yield 39.4%.

A corresponding extraction was carried out in the presence of cellulase by adding an amount of GC440 cellulase corresponding to 0.036% of the weight of the groats to the ground wheat. The extraction time was 60 h. The total activity of the amount of wheat used was 1280 kDP°. 10080 ml of extract with an activity of 72 DP°/ml was obtained by separating the extract with a sieve. The total activity of the extract obtained was thus 725.8 kDP°/ml and the extract yield 56.7%.

The results show that addition of cellulase to the extraction water considerably increases the yield of β-amylase.

EXAMPLE 6

The effect of cellulase on the yield of β-amylase from polished wheat was studied. Wheat was polished with a rice polishing machine by breaking the surface and removing the outermost part, i.e. most of the pericarp was removed and the testa slightly damaged. 10 kg of polished wheat with β-amylase activity of 128 DP°/g was extracted in 15 litres of water containing 0.5% sodium metabisulphite and 0.5% of sodium-sulphite. The extraction was carried out at 30° C. either without cellulase or in the presence of cellulase.

The extraction time without cellulase was 72 h. The total activity of the amount of wheat used was 1280 kDP°. 9780 ml of extract with an activity of 15 DP°/ml was obtained by separating the extract with a sieve. The total activity of the extract obtained was thus 146.7 kDP°/ml and the extract yield 11.5%.

A corresponding extraction was carried out in the presence of cellulase by adding an amount of GC440 cellulase corresponding to 0.036% of the weight of the polished wheat to the ground. The extraction time was 60 h. The total activity of the amount of wheat used was 1280 kDP°. 9250 ml of extract with an activity of 35 DP°/ml was obtained by separating the extract with a sieve. The total activity of the extract obtained was thus 323.8 kDP°/ml and the extract yield 25.3%.

The results show that addition of cellulase to the extraction water considerably increases the yield of β-amylase.

EXAMPLE 7

500 g hulled wheat (moisture 13%) and 750 ml of water (30° C.) was mixed for 10 minutes in an Ultra Turrax mixer to obtain a thick slurry. The slurry was centrifuged for 15 minutes at 200 rpm (1859 G) to separate A-starch. The separated starch was removed (590 g).

The remaining lighter fraction containing the aqueous phase, proteins and B-starch altogether 560 ml was thoroughly mixed and divided into two portions. Cellulase ROHALASE® SEP was added into one portion in the amount of 0.25 ml/kg d.s. (on dry substance) and the other portion was a control sample without enzyme addition.

The β-amylase activity (DP°) was measured from both the samples after incubation at about 25° C. for 0 0.5, 1 and 2 hours and the extraction % of β-amylase based on the β-amylase of hulled wheat was calculated. The results are shown in Table 3.

TABLE 3

| | Test | | | |
|---|---|---|---|---|
| | DP°/g | DP°/ml | Total acitivty DP° | β-amylase extraction % |
| Hulled wheat | 81 | | 40500 | |
| 0 h control | | 26 | 14560 | 36 |
| 0.5 h control | | 40 | 22400 | 55 |
| 0.5 h Rohalse ® SEP | | 44 | 24640 | 61 |
| 1.0 h control | | 44 | 24640 | 61 |
| 1.0 h Rohalse ® SEP | | 53 | 29680 | 73 |
| 2.0 h control | | 47 | 26320 | 65 |
| 2.0 h Rohalse ® SEP | | 52 | 29120 | 72 |

What is claimed is:

1. A method of extracting β-amylase from a cereal, the method comprising:
   (a) providing a composition comprising a cereal in an aqueous medium, wherein the cereal is an ungerminated cereal grain selected from the group consisting of barley, wheat, and rye;
   (b) extracting the composition of step (a) in the presence of an enzyme preparation to obtain an extract containing β-amylase, wherein the enzyme preparation comprises cellulase, hemicellulase, and β-glucanase activities in the aqueous medium; and, then
   (c) recovering β-amylase in purified form from the extract of step (b).

2. The method of claim 1, wherein the cereal is barley or wheat.

3. The method of claim 1, wherein the cereal further comprises pretreated grains of said cereal and wherein said pretreated grains are pretreated by a process selected from the group consisting of removing of husk, bran, starch, or gluten; milling; grinding; polishing; and combinations thereof.

4. The method of claim 3, wherein the cereal is barley, wherein the pretreated grains of the cereal comprises a husked barley, and wherein the husked barley is provided by removing of husk from a grain of said barley.

5. The method of claim 4, wherein the husked barley further comprises a husked barley having a substantially intact endosperm.

6. The method of claim 5, wherein in the process of removing of husk from the cereal no more than 20% of the weight of the barley cereal is removed.

7. The method of claim 1, wherein the extracting is carried out in reducing conditions, and wherein said reducing conditions are capable of releasing β-amylase bound to structural protein of the cereal.

8. The method of claim 7, wherein said reducing conditions are provided by water containing $SO_2$.

9. The method of claim 4, wherein said husked barley is extracted with an aqueous medium comprising water and $SO_2$ and wherein the ratio of husked barley to aqueous medium is from 5:8 to 2:3 (w/v).

10. The method of claim 1, wherein in step (b) extracting is carried out at a temperature of 25 to 35° C.

11. The method of claim 10, wherein said temperature is 29 to 31° C.

12. The method of claim 1, wherein said extracting comprises extracting for 48 to 66 hours.

13. The method of claim 12, wherein said extracting comprises extracting for 55 to 62 hours.

14. The method of claim 1, wherein in step (b) extracting in the presence of an enzyme preparation comprises adding an enzyme preparation to the composition of step (a) at a concentration of enzyme versus cereal of at least 0.015% by weight (w/w).

15. The method of claim 14, wherein adding said enzyme preparation to said composition of step (a) comprises adding the enzyme preparation at a concentration corresponding to an enzyme activity selected from the group comprising:
   (i) at least 1050 Units (U) of dinitrosalicylic acid carboxymentyl cellulose (DNS-CMC) cellulase activity per kilogram of cereal;
   (ii) at least 900 U of β-glucanase activity per kilogram of cereal; and,
   (iii) at least 285 U of dinitrosalicylic acid xylanase (DNS-xylanase) activity per kilogram of cereal; and,
wherein the enzyme preparation is the cellulase enzyme GC 440 obtained from *Trichoderma longibrachiatum*.

16. The method of claim 1, wherein said enzyme preparation comprises a cellulase of a mold.

17. The method of claim 16, wherein said mold is a mold selected from the group consisting of the genera *Humicola, Fusarium, Myceliopthora, Aspergillus, Penicillium, Trichoderma*, and combinations thereof.

18. The method of claim 16, wherein said cellulase is a cellulase of *Trichodernia* mold.

19. The method of claim 1, further comprising the step of producing starch from said cereal.

20. The method of claim 19, wherein said β-amylase is extracted from the composition of step (a) before separating starch from said cereal.

21. The method of claim 19, wherein said β-amylase is extracted from the composition of step (a) after separating starch from said cereal.

22. The method of claim 1, wherein said enzyme preparation increases the yield of β-amylase obtainable from said cereal.

23. The method of claim 22, wherein the yield of β-amylase is between about 10 and 15% higher than without said cellulase present.

24. The method of claim 1, wherein said recovering β-amylase from said medium comprises removing β-amylase from said medium in purified and concentrated form by pressure filtration and ultra filtration.

25. A method of extracting β-amylase from barley, comprising the steps of:
   a) providing an aqueous medium containing grains of barley in ungerminated form;
   b) providing a cellulase enzyme preparation having at least cellulase, hemicellulase, and β-glucanase activities in said aqueous medium;
   c) extracting β-amylase from said grains to provide an aqueous extract containing β-amylase;
   d) recovering β-amylase in purified form from said aqueous extract; and
   e) optionally subjecting said recovered β-amylase of step (d) to further processing, said processing selected from purifying, concentrating, and combinations thereof.

26. The method of claim 25, wherein the β-amylase yield is as much as 65% of the total amount of β-amylase in said barley.

* * * * *